United States Patent
Rajebi

(10) Patent No.: US 10,271,837 B1
(45) Date of Patent: Apr. 30, 2019

(54) ARTERIOTOMY CLOSURE DEVICE

(71) Applicant: Mohammad Reza Rajebi, Naples, FL (US)

(72) Inventor: Mohammad Reza Rajebi, Naples, FL (US)

( * ) Notice: Subject to any disclaimer, the term of this patent is extended or adjusted under 35 U.S.C. 154(b) by 0 days.

(21) Appl. No.: 16/194,642

(22) Filed: Nov. 19, 2018

(51) Int. Cl.
*A61B 17/04* (2006.01)
*A61B 17/34* (2006.01)
*A61B 17/128* (2006.01)
*A61B 17/12* (2006.01)

(52) U.S. Cl.
CPC ...... *A61B 17/0469* (2013.01); *A61B 17/1285* (2013.01); *A61B 17/3403* (2013.01); *A61B 17/3415* (2013.01); *A61B 17/12009* (2013.01); *A61B 2017/0472* (2013.01); *A61B 2017/3405* (2013.01)

(58) Field of Classification Search
CPC .......... A61B 17/0469; A61B 2017/047; A61B 2017/0472; A61B 2017/0477; A61B 2017/0475; A61B 17/12009; A61B 17/1285; A61B 17/3403; A61B 2017/3405; A61B 17/3415
See application file for complete search history.

(56) References Cited

U.S. PATENT DOCUMENTS

| | | | | |
|---|---|---|---|---|
| 5,320,632 A | * | 6/1994 | Heidmueller | A61B 17/0469 112/169 |
| 5,364,408 A | * | 11/1994 | Gordon | A61B 17/0469 112/169 |
| 5,374,275 A | * | 12/1994 | Bradley | A61B 17/0469 606/139 |
| 5,417,699 A | * | 5/1995 | Klein | A61B 17/0057 112/169 |
| 5,458,609 A | * | 10/1995 | Gordon | A61B 17/0469 112/169 |
| 5,470,338 A | * | 11/1995 | Whitfield | A61B 17/0469 112/169 |

(Continued)

OTHER PUBLICATIONS

Author: Khan Academy MedicinePublished on May 2, 2014Title: Patent ductus arteriosus | Circulatory System and Disease | NCLEX-RN | Khan Academy https://www.youtube.com/watch?v=IZSi0xifXwc.

*Primary Examiner* — David C Eastwood
(74) *Attorney, Agent, or Firm* — Global Intellectual Property Agency, LLC; Daniel Boudwin

(57) ABSTRACT

An arteriotomy closure device. The arteriotomy closure device includes a proximal end and a distal end designed to be inserted into an arteriotomy opening resulting from an endovascular procedure. The arteriotomy closure device provides a pair of doors operated by a door drive that stabilize the arteriotomy closure device within an artery during a closure operation. A plurality of needles with a suture attached to each penetrate the arterial wall. When the needles are engaged with a plurality of needle receptors, a cap trap is engaged with the needle receptors so that when the needles are retracted, the suture is secured in a position to close the arteriotomy opening. When the needles are retracted, the doors are lowered and the arteriotomy closure device is removed from the closure site, the suture is used to close the arteriotomy opening.

12 Claims, 8 Drawing Sheets

(56) References Cited

U.S. PATENT DOCUMENTS

| | | | | |
|---|---|---|---|---|
| 5,527,321 | A  * | 6/1996 | Hinchliffe | A61B 17/0469 112/169 |
| 5,575,800 | A | 11/1996 | Gordon | |
| 6,048,351 | A  * | 4/2000 | Gordon | A61B 17/0469 112/169 |
| 7,935,128 | B2 * | 5/2011 | Rioux | A61B 17/0469 606/144 |
| 9,241,707 | B2 * | 1/2016 | Roorda | A61B 17/0469 |
| 2001/0031973 | A1 * | 10/2001 | Nobles | A61B 17/0057 606/144 |
| 2002/0173800 | A1 * | 11/2002 | Dreyfuss | A61B 17/0057 606/139 |
| 2003/0028201 | A1 * | 2/2003 | Navarro | A61B 17/0057 606/139 |
| 2007/0213757 | A1 * | 9/2007 | Boraiah | A61B 17/0057 606/184 |
| 2009/0312772 | A1 * | 12/2009 | Chu | A61B 17/0469 606/144 |
| 2014/0148825 | A1 * | 5/2014 | Nobles | A61B 17/0469 606/145 |
| 2014/0350576 | A1 * | 11/2014 | Patel | A61B 17/0482 606/145 |
| 2018/0221015 | A1 * | 8/2018 | Bhalla | A61B 17/0469 |

* cited by examiner

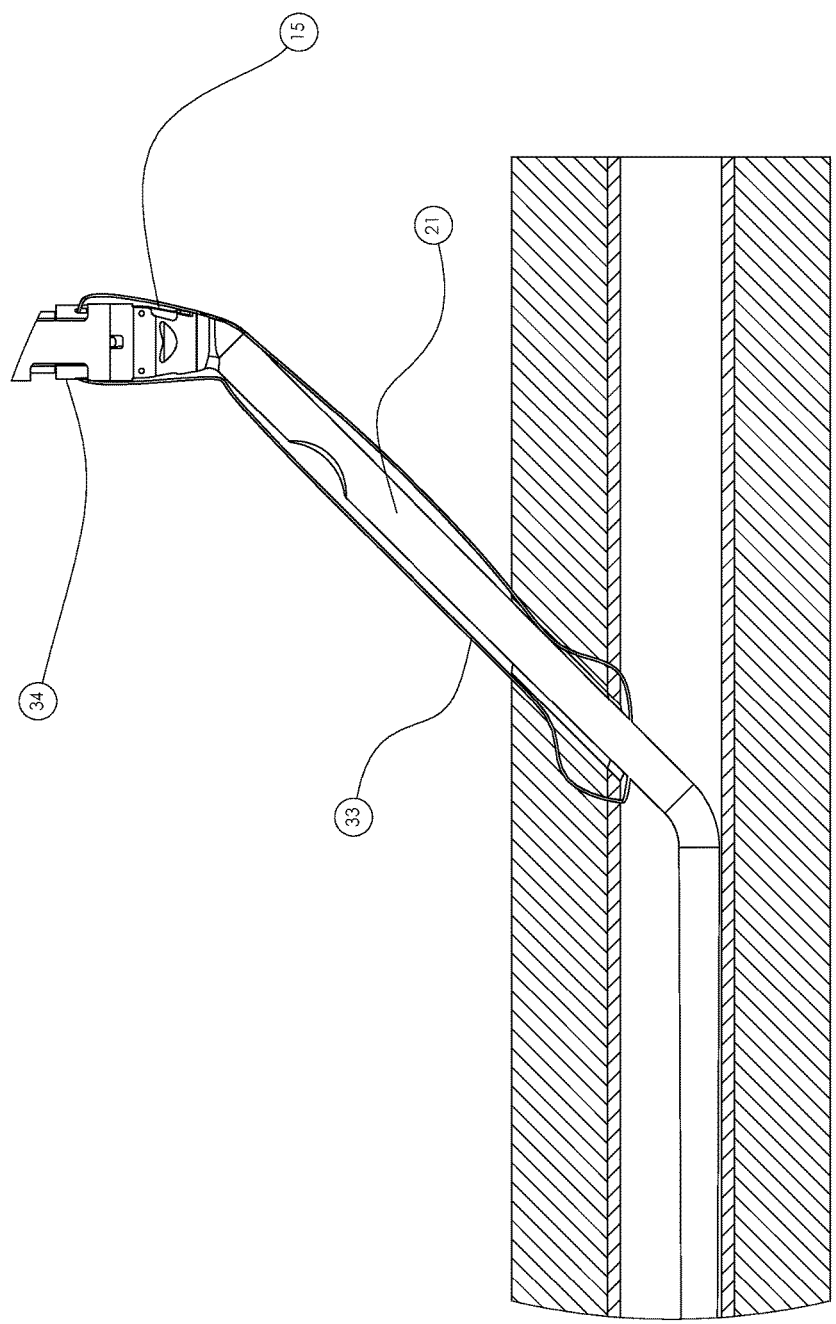

ARTERIOTOMY CLOSURE DEVICE

BACKGROUND OF THE INVENTION

The present invention relates to an arteriotomy closure device. Arteriotomy refers to an opening or cut in an artery wall. Additionally, arteriotomy is a common step in many endovascular procedures to treat conditions such as abdominal aortic aneurysm and cardiac valve replacement. Typically, these openings are made with a small needle under ultrasonographic guidance and then dilated to the desired size using sequential dilators.

Different procedures may require openings of various sizes to be placed into an artery of a patient. A closing strategy is needed when these procedures are conducted. Performing arteriotomy procedures without a closing strategy may result in excess, unnecessary blood loss. This risk is stronger in procedures that require a larger opening to be made, such as transcatheter aortic valve replacement (TAVR).

Currently available devices that seek to provide closing strategies for arteriotomy procedures are primarily utilized in procedures that involve small openings. Because of the increase of need for procedures involving large openings in arteries and the relative ineffectiveness of currently available devices, there is a need for a device that provides effectiveness when closing a large arteriotomy following an arterial procedure.

SUMMARY OF THE INVENTION

In view of the foregoing disadvantages inherent in the known types of arteriotomy closure devices now present in the prior art, the present invention provides an arteriotomy closure device wherein the same can be utilized for providing convenience for the user when closing an opening following an arterial procedure.

The present system comprises a body defining a proximal end opposite of a distal end. The distal end is configured to be inserted into an artery. A door driver is engaged with the body at the proximal end of the body. The door driver is in operable connection with a pair of doors disposed on an external surface of the distal end of the body. The pair of doors are configured to open inside of the artery. A plurality of needles is disposed in a plurality of needle shafts in the body and are configured to extend through a corresponding plurality of needle openings disposed on an external surface of the distal end of the body. A suture is disposed on the body such that the suture is connected at a first end to a needle of the plurality of needles adjacent to the first door and connected at a second end to a needle of the plurality of needles adjacent to the second door. A plurality of needle receptors is disposed on an external surface of the distal end of the body. Each needle receptor is configured to receive a needle of the plurality of needles that is corresponding thereto. A needle actuator is disposed on an external surface of the proximal end of the housing. The needle actuator is configured to release the plurality of needles into the plurality of needle receptors. A cap trap is configured to hold the first end and the second end of the suture in the plurality of needle receptors when the plurality of needles is retracted.

It is therefore an object of the present invention to provide a new and improved arteriotomy closure device that has all of the advantages of the known art and none of the disadvantages.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 7 shows a perspective view of an embodiment of the arteriotomy closure device in use.

DETAILED DESCRIPTION OF THE INVENTION

Figure 1:
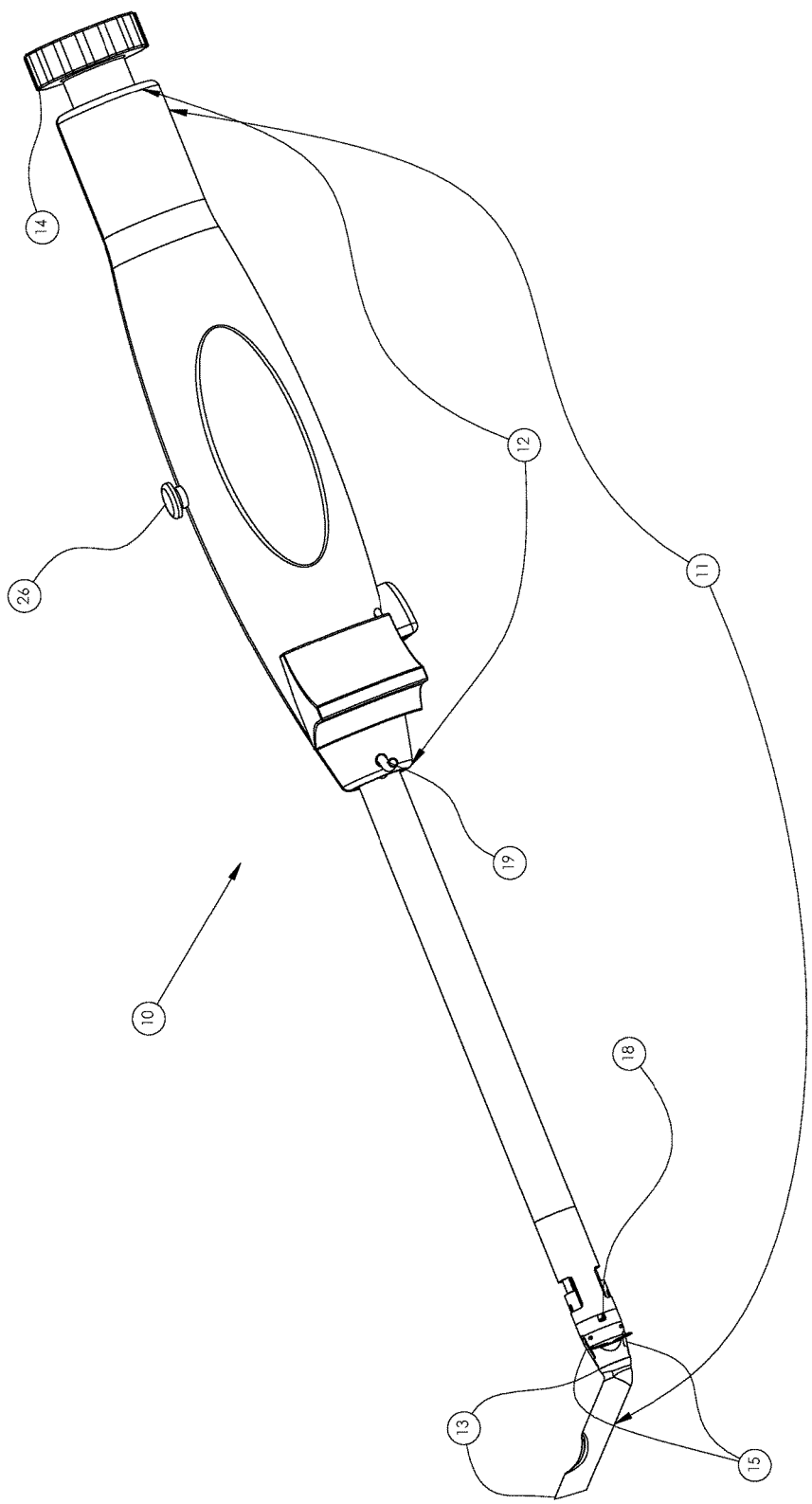
FIG. 1 shows a perspective view of an embodiment of the arteriotomy closure device.

Reference is made herein to the attached drawings. Like reference numerals are used throughout the drawings to depict like or similar elements of the arteriotomy closure device. The figures are intended for representative purposes only and should not be considered to be limiting in any respect.

Referring now to FIG. 1, there is shown a perspective view of an embodiment of the arteriotomy closure device. The arteriotomy closure device 10 comprises a body 11 shaped to be held in a hand of an operator and insertable into an arteriotomy. The body 11 is defined by a proximal end 12 disposed oppositely a distal end 13. The body 11 is configured to be inserted into an artery that is in need of closure. The distal end 13 is configured to enter a bloodstream of a patient and is a sanitized material. The proximal end 12 will not enter the bloodstream of a user but provides a housing upon which several elements configured for manipulation in order to actuate the various structural components of the device are located. In one embodiment, the body is ergonomic, such that convenience is provided to an operator of the arteriotomy closure device 10 wherein the arteriotomy closure device 10 is easier to grasp by the hand of the operator.

A door driver 14 is extends from the body 11 at the proximal end 12. In the illustrated embodiment, the door driver extends laterally from the proximal end 12 of the arteriotomy closure device 10 such that when the body 11 is held in the hand of the operator, the thumb may operate the door driver. The door driver 14 is in operable connection with a pair of doors 15.

In one specific embodiment, the door driver 14 is arranged such that rotation of the door driver 14 along a rotational axis freely moves the pair of doors 15 between a lowered position and a raised position. For example, in one embodiment, the door driver 14 comprises a threading corresponding to a threading in a door driver cavity internally disposed in the body 11 at the proximal end 12. Rotation of the door driver 14 in a first direction around the rotational axis exerts force upon a door rod, placing the pair of doors 15 into a raised position, while rotation of the door driver 14 in a second direction around the rotational axis exerts a pulling force upon the door rod and places the pair of doors 15 into a lowered position. As such, convenience is provided to the operator where operating the pair of doors 15.

In another embodiment, the arteriotomy closure device 10 further comprises a blood indicator tube 17. The blood indicator tube 17 is defined by a blood indicator tube inlet 18 disposed oppositely a blood indicator tube outlet 19. When the arteriotomy closure device 10 is inserted into an artery, blood will flow from the artery into the blood indicator tube 17 through the blood indicator tube inlet 18 and outward from the blood indicator tube outlet 19 such as to confirm entry of the distal end 13 of the arteriotomy closure device 10 into the artery from an external view of a patient.

Figure 2:
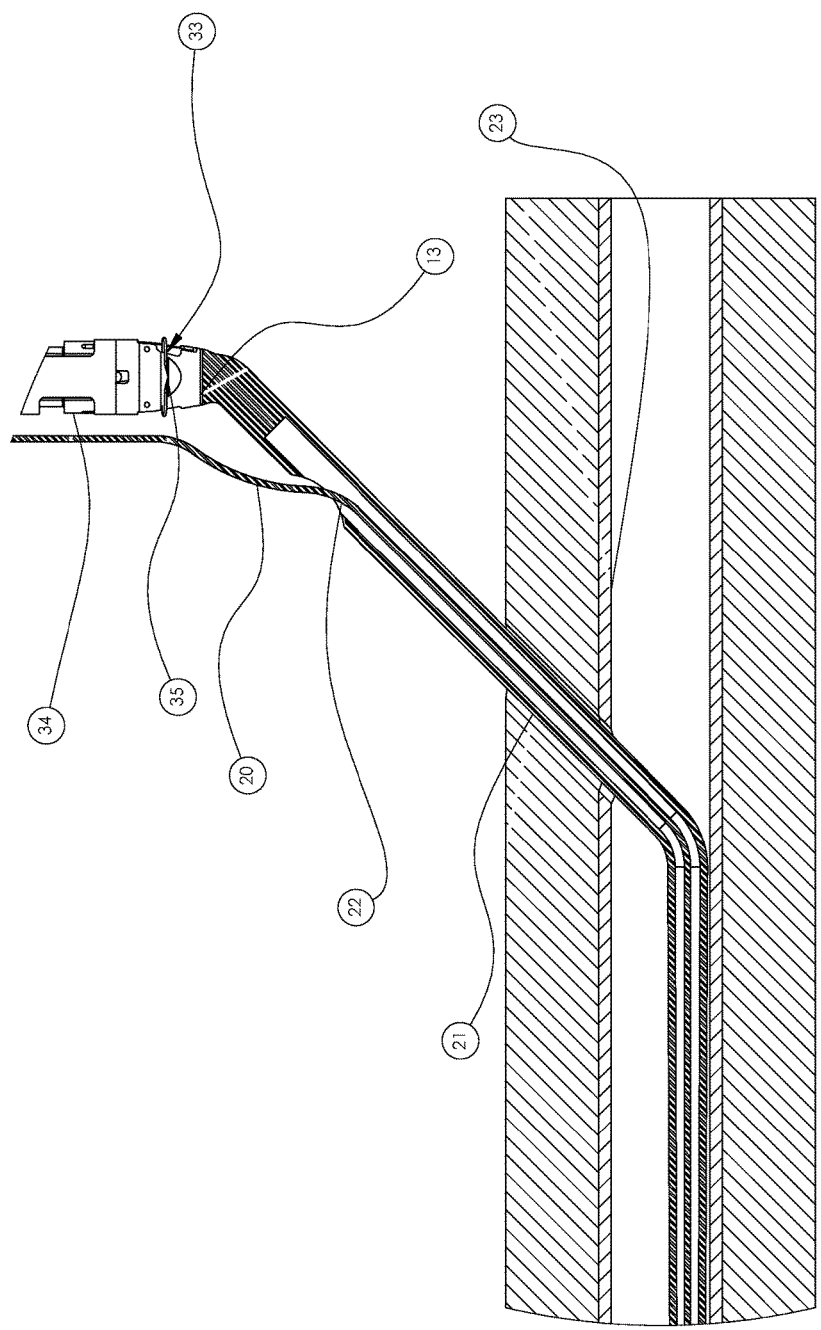
FIG. 2 shows a cross-sectional view of a distal end of an embodiment of the arteriotomy closure device in use.

Referring now to FIG. 2, there is shown a cross-sectional view of an embodiment of the distal end of the arteriotomy closure device in use. In one embodiment, the distal end 13 of the arteriotomy closure device comprises a guide wire 20 and a guide wire boot 21. The guide wire boot 21 is flexible, such that the guide wire 20 may be utilized to position the guide wire boot 21 into a desired position. Manipulation of the guide wire boot 21 by the guide wire 20 allows for the distal end 13 to be routed into position within an artery of a patient. In the illustrated embodiment, the guide wire boot 21 is hollow and the guide wire 20 is disposed in the guide wire boot 21 through a distal end and extends from an aperture 22 disposed in a proximal end of the guide wire boot 21. The guide wire 20 and the guide wire boot 21 provide convenience to the operator of the arteriotomy closure device by allowing for the operator to more effectively and accurately position the distal end of the arteriotomy closure device 10.

Figure 3A:
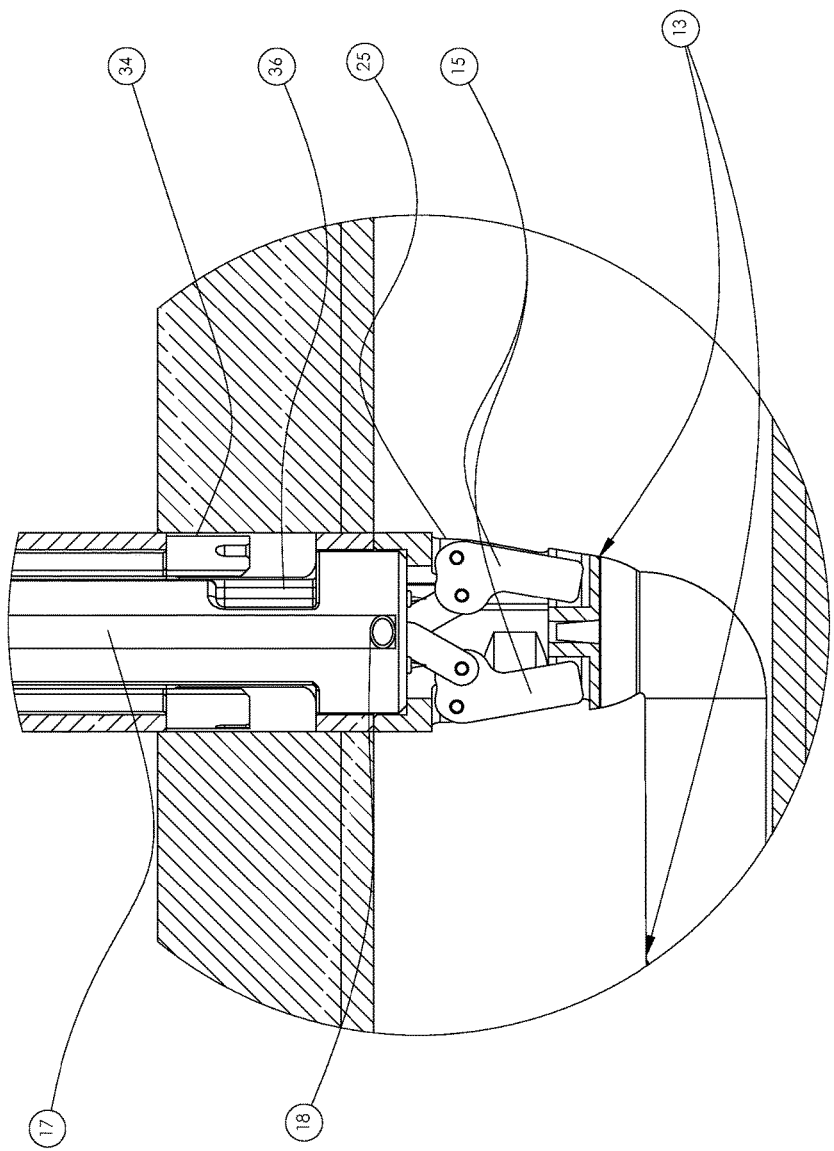
FIG. 3A shows a cross-sectional view of a distal end of an embodiment of the arteriotomy closure device in use.
Figure 3B:
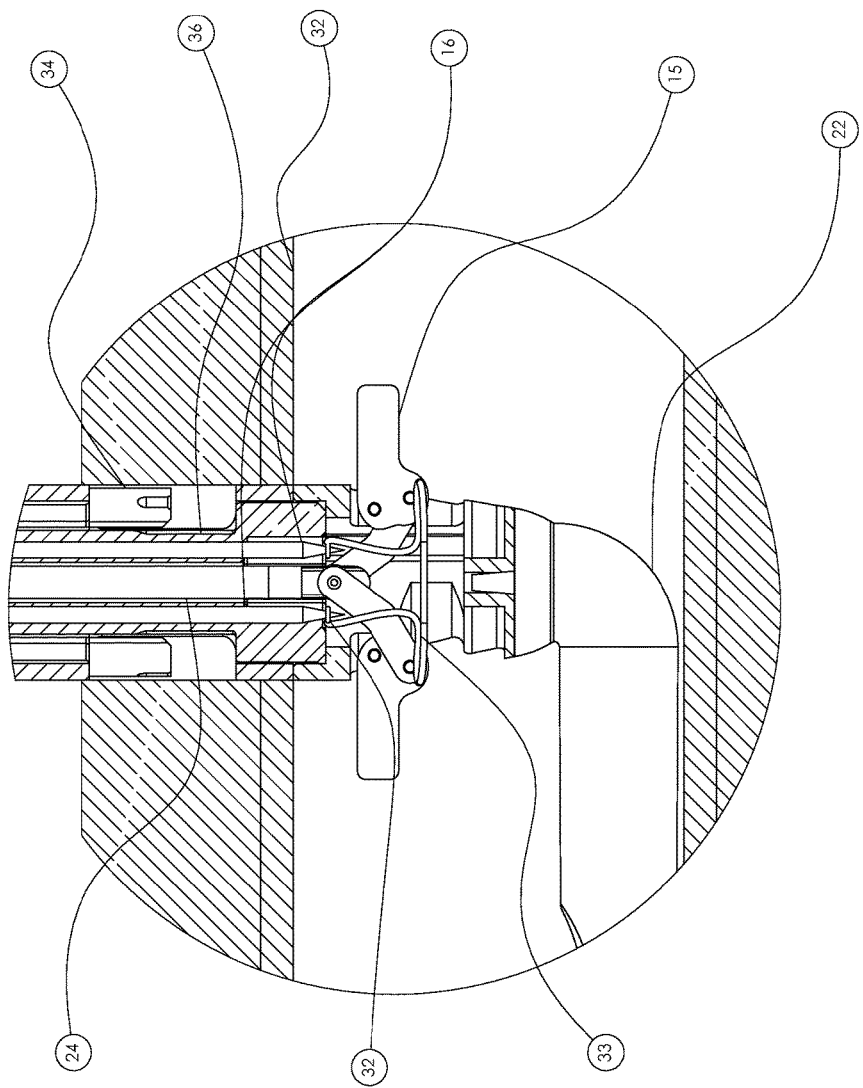
FIG. 3B shows a cross-sectional view of a distal end of an embodiment of the arteriotomy closure device in use.

Referring now to FIGS. 3A and 3B, there are shown cross-sectional views of an embodiment of the distal end of the arteriotomy closure device in use. Once the distal end 13 of the arteriotomy closure device 10 is inserted into an artery, the pair of doors 15 are lifted from a lowered position, shown in FIG. 3A, to a raised position, shown in FIG. 3B. Once the pair of doors 15 are oriented into the raised position, such as by rotation of the door driver 14, the doors 15 are moved into contact with an arterial wall 23. A hard stop mechanism is operably integrated upon the door driver 14, such that the operator will receive feedback therefrom when the doors 15 are fully placed into the raised position wherein the door driver 14 will not be movable beyond the hard stop mechanism.

In one embodiment, the door driver is rotated such that a door rod 24 is forced downward and the linkage system is actuated. In the illustrated embodiment, the linkage system is defined where the pair of doors 15 are each hingedly affixed to the door rod opposite the door driver, such that downward orientation of the door rod pushes upon the hinges and swings each of the pair of doors 15 outward relative to a pair of door housings 25 corresponding to each of the pair of doors 15. In the illustrated embodiment, each of the pair of doors 15 is parallel with the distal end 13 of the arteriotomy closure device 10 when in the lowered position, as shown in FIG. 3A, and each of the pair of doors 15 is perpendicular with the arteriotomy closure device 10 when in the raised position, as shown in FIG. 3B.

When the doors are moved into contact with the arterial wall 23, a seal is formed between the arterial wall 23 and the blood indicator tube inlet 18, as well as by tension exerted by the pair of doors 15, such that blood will flow at a visibly reduced rate into the blood indicator tube through the blood indicator tube inlet 18. As such, the operator will be notified of the successful creation of the seal by the absence of blood flow through the blood indicator tube outlet.

The arteriotomy closure device comprises a plurality of needles 16. The plurality of needles 16 are each made of a flexible material, such as nitinol, such that the needles are held in a straightened position when in a stored position in the plurality of needle shafts, as shown in FIG. 3B. In one embodiment, the plurality of needles 16 comprises four needles. The plurality of needles 16 each comprise a sharpened end configured to penetrate the arterial wall 23 during closure. In the illustrated embodiment, a suture ring 32 is attached to a tip portion of each needle of the plurality of needles 16. In one embodiment, the pair of doors 15 each comprises at least one recess thereon, such that each door of the pair of doors 15 will accommodate the plurality of needles 16 when passing adjacent to or through the pair of doors 15.

Figure 4:
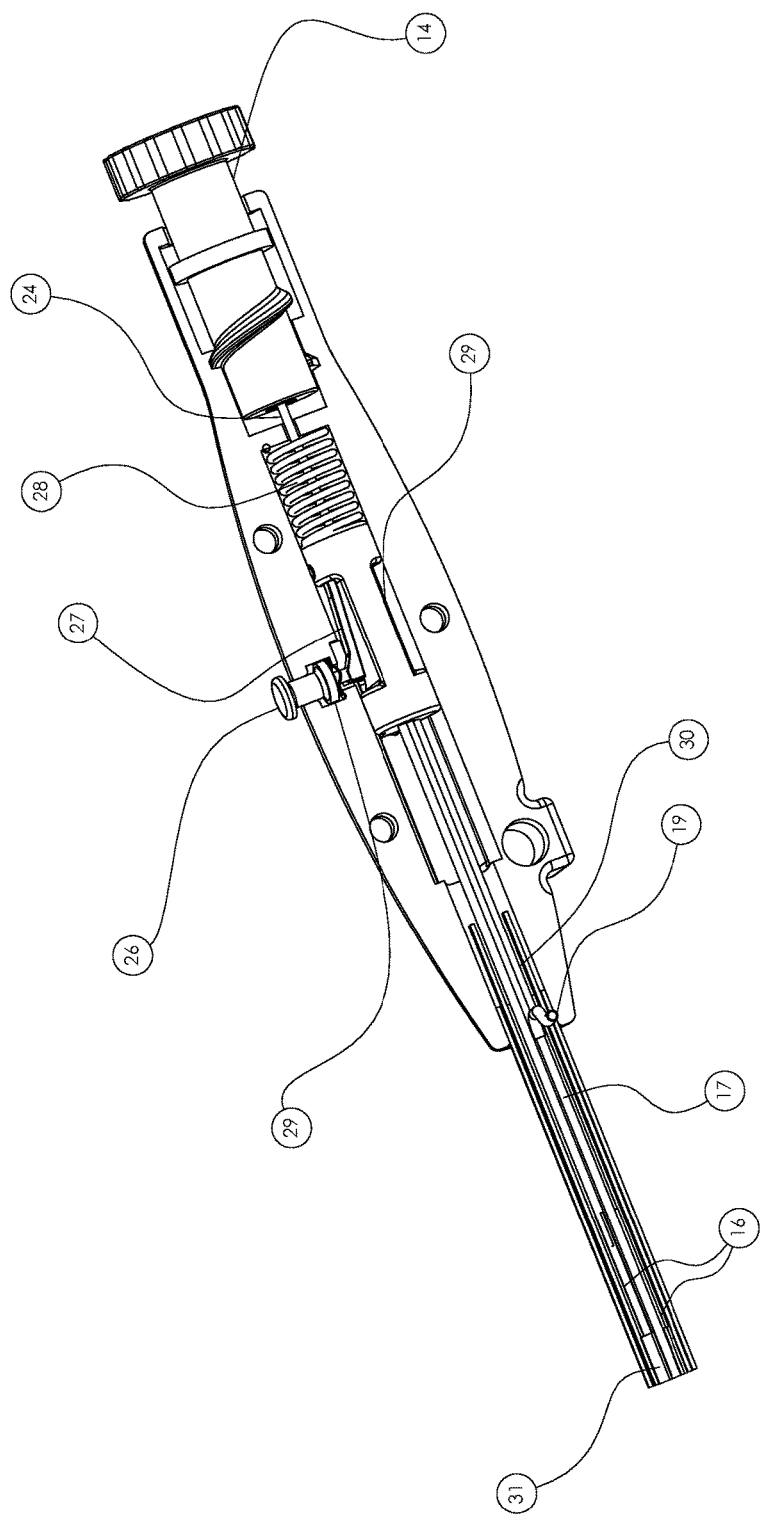
FIG. 4 shows a cross-sectional view of an embodiment of the arteriotomy closure device in use.

Referring now to FIG. 4, there is shown a cross-sectional view of an embodiment of the arteriotomy closure device in use. The plurality of needles 16 is in operable connection with a needle actuator 26 disposed on an external surface of the proximal end 12 of the body 11. In the illustrated embodiment, the needle actuator 26 is a latch button.

In the illustrated embodiment, the latch button 26 is operably mounted upon a piston latch 27, such that actuation of the latch button 26 will cause actuation of the piston latch 27. When the piston latch 27 is actuated, a piston spring 28 is released. The piston spring 28 is disposed in the body 11 and is in operable connection with the piston driver 29. When the piston driver 29 is released, the pressure exerted by the force of the piston spring 28 is applied to the piston driver 29, such that force is exerted upon a plurality of piston rods 30 and therethrough to a needle piston 31. The needle piston 31 is in operable connection with the plurality of needles 16, such that the plurality of needles 16 are expelled through the needle openings in the distal end 13 of the body 11 when force is exerted upon the needle piston 31.

Figure 5:
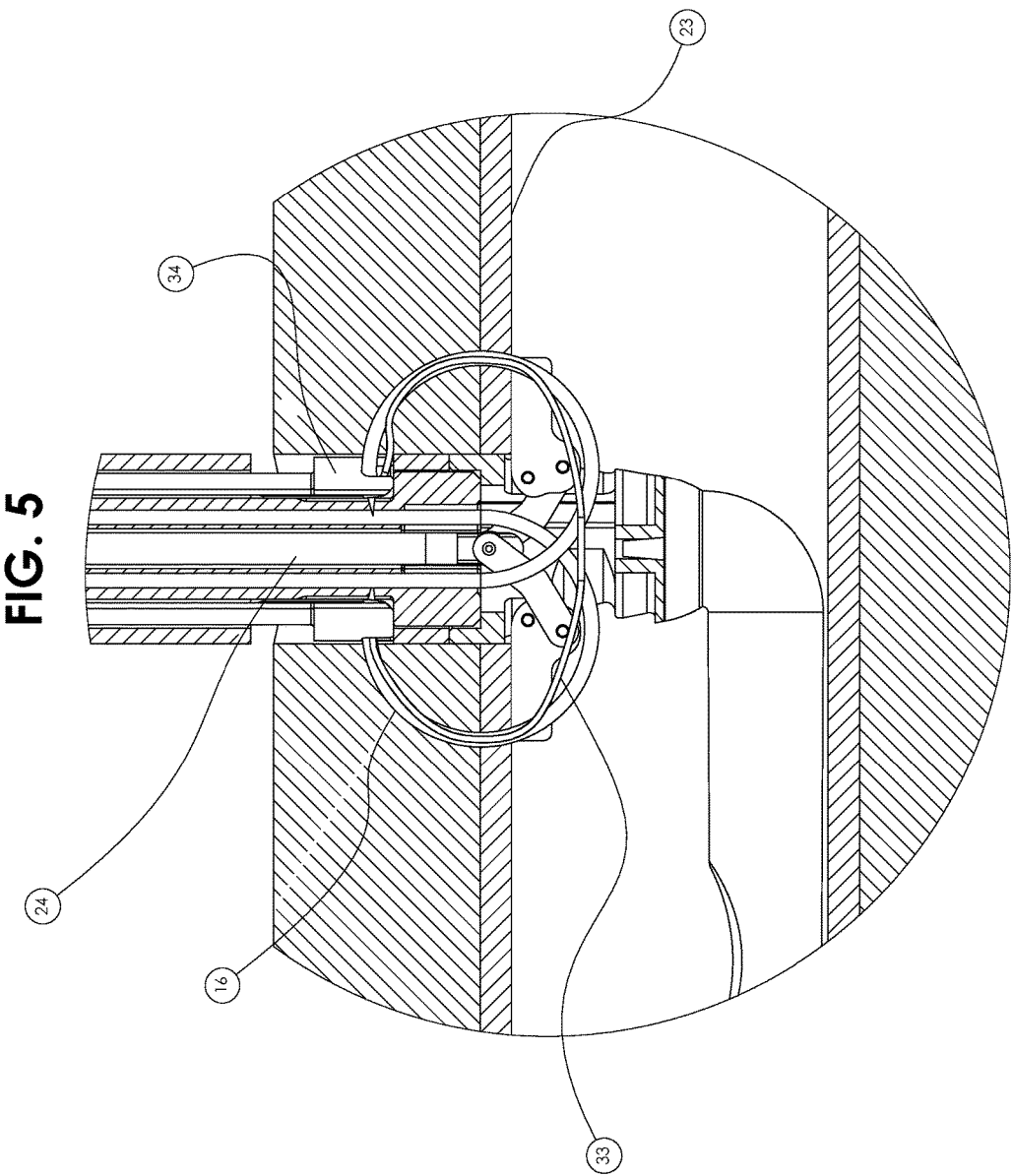
FIG. 5 shows a cross-sectional view of an embodiment of the arteriotomy closure device in use.

Referring now to FIG. 5, there is shown a cross-sectional view of a distal end of an embodiment of the arteriotomy closure device. When force is exerted upon the needle piston, the plurality of needles 16 are each expelled through the corresponding needle openings in the distal end 13 of the arteriotomy closure device 10. The plurality of needles 16 are biased in a curved position, such that as each of the plurality of needles 16 extends from the corresponding needle opening, the sharpened end of each needle of the plurality of needles 16 is guided toward a needle receptor in the distal end 13 of the body 11.

A plurality of sutures 33 is attached to each needle of the plurality of needles 16, such that the suture 33 is pulled through the cavity created by the plurality of needles 16 as they penetrate the arterial walls 23 of the patient. Each suture of the plurality of sutures comprises a first end and a second end. The first end of each suture is attached to a needle of the plurality of needles 16 adjacent to a first door of the pair of doors while a second end of each suture is attached to a corresponding needle on a second door of the pair of doors. In the illustrated embodiment, the plurality of sutures 33 are attached to each needle via a suture ring. The plurality of needle receptors is each in operable connection with a cap trap 34.

The cap trap 34 is configured to be slid into a downward position, as shown, toward the distal end 13 of the arteriotomy closure device 10 and away from the proximal end of the arteriotomy closure device 10, by the operator. When the cap trap 34 is slid into engagement with the plurality of needle receptors, the suture rings are retained in the needle receptors. As the plurality of needles 16 is retracted by retraction of the needle actuator, the suture rings are retained in the needle receptors, and the sutures 33 are held by the suture rings such that the sutures 33 remain held in the cavities created by the penetration of the arterial wall 23 by the plurality of needles 16.

Figure 6:
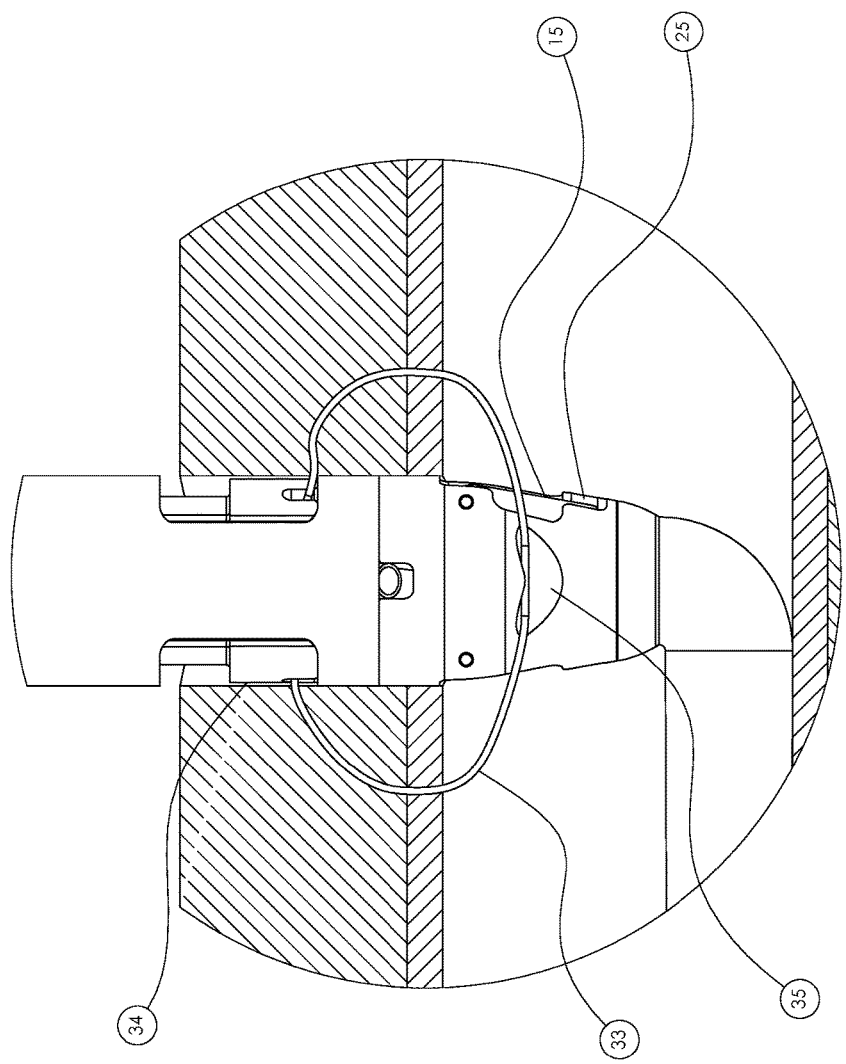
FIG. 6 shows a cross-sectional view of an embodiment of the arteriotomy closure device in use.

Referring now to FIG. 6, there is shown a cross-sectional view of a distal end of an embodiment of the arteriotomy closure device. When the plurality of needles is returned to the stored position in the needle shafts, the pair of doors 15 may be placed into the lowered position, such that the pair of doors 15 are each disposed in the pair of corresponding door housings 25. In the illustrated embodiment, the pair of doors 15 are placed into the lowered position by reversing the door driver, such as by rotating the door driver in the second direction around the rotational axis.

In the illustrated embodiment, the sutures 33 are disposed in an opening 35 at the distal end 13 of the body, such that the loops formed by the sutures 33 will remain in the artery as the arteriotomy closure device 10 is removed from the arteriotomy opening.

Referring now to FIG. 7, there is shown a perspective view of an embodiment of the arteriotomy closure device in use. The sutures 33 are stored in the opening such that the sutures 33 will provide slack as the arteriotomy closure device 10 is removed from the patient. When the arteriotomy closure device 10 is removed from the patient, the sutures 33 will extend such that excess portions thereof may be utilized to secure the closure site. The sutures 33 may be cut at any length after being removed from the closure site. After being trimmed, the sutures 33 can be tensioned and affixed together, such that the arteriotomy is secured shut.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An arteriotomy closure device, comprising:
    a body having a proximal end and a distal end;
    the distal end configured to be inserted into an artery;
    a door driver in operable connection with a pair of doors, such that the door driver is configured to move the pair of doors between a raised position and a lowered position;
    the pair of doors disposed in a pair of door housings on an external surface of the body at the distal end thereof;
    a plurality of elongate needles disposed in a plurality of needle shafts of the body;
    a plurality of needle openings disposed adjacent to the pair of doors; the plurality of needle openings configured to enable the plurality of needles to extend therethrough;
    a suture having a first end and a second end, the first end attached to a first needle of the plurality of elongate needles and the second end attached to a second needle of the plurality of elongate needles, the second needle opposing the first needle;
    a plurality of needle receptors on the external surface of the body; wherein each receptor corresponds to each needle and is configured to receive a corresponding needle therein;
    a needle actuator disposed on an external surface of the body; the needle actuator configured to expel and retract the plurality of needles through the plurality of needle openings;
    wherein the plurality of needles are each biased in a curved configuration such that the plurality of needles will bend toward the plurality of needle receptors as they are expelled through the plurality of needle openings;
    a cap trap slidably disposed on an external surface of the distal end of the body; the cap trap configured to hold the plurality of sutures in the plurality of needle receptors as the plurality of needles are retracted.

2. The arteriotomy closure device of claim 1, wherein:
    the door driver is in operable connection with a door rod;
    the door driver comprises a threading corresponding to a threading in a door driver cavity internally disposed in the proximal end of the body;
    wherein rotation of the door driver in a first direction around a rotational axis exerts downward force upon the door rod;
    the door rod in operable connection with the pair of doors via a linkage system.

3. The arteriotomy closure device of claim 2, wherein the linkage system is defined by the pair of doors being hingedly affixed to the door rod opposite the door driver.

4. The arteriotomy closure device of claim 2, wherein the threading defines a hard stop mechanism upon the door driver.

5. The arteriotomy closure device of claim 1, wherein the needle actuator comprises:
    a latch button disposed on an external surface of the proximal end of the body;
    the latch button operably mounted upon a piston latch disposed in the proximal end of the body;
    the piston latch operably attached to a piston spring, such that depression of the piston latch will release the piston spring;
    the piston spring configured to exert tension upon a piston driver;
    the piston driver in operable connection with the plurality of needles, such that the piston driver expels the plurality of needles through the plurality of needle openings.

6. The arteriotomy closure device of claim 1, wherein the distal end comprises a guide wire in operable connection with a flexible guide wire boot.

7. The arteriotomy closure device of claim 1, further comprising a blood indicator tube having a blood indicator tube inlet disposed opposite a blood indicator tube outlet, wherein the blood indicator tube inlet is disposed on the distal end of the body and the blood indicator tube outlet is disposed on the proximal end of the body.

8. The arteriotomy closure device of claim 1, wherein the suture comprises a suture ring disposed at each of the first end of the suture and the second end of the suture, wherein each suture ring is configured to be secured in a needle receptor of the plurality of needle receptors by the cap trap.

9. The arteriotomy closure device of claim 1, wherein the suture is bioabsorbable.

10. The arteriotomy closure device of claim 1, wherein the distal end of the body is made of a flexible material.

11. The arteriotomy closure device of claim 1, wherein the plurality of needles are each made of nitinol.

12. The arteriotomy closure device of claim 1, wherein the body is ergonomic.

\* \* \* \* \*